(12) United States Patent
Gaillet et al.

(10) Patent No.: US 10,571,255 B2
(45) Date of Patent: Feb. 25, 2020

(54) DEVICE FOR MEASURING A SHAPE OF A WALL PORTION OF A COKE OVEN

(71) Applicant: Centre de Pyrolyse du Charbon de Marienau, Forbach (FR)

(72) Inventors: Jean Paul Gaillet, Petit-Ebersville (FR); David Glijer, Metz (FR); Damien Streiff, Porcelette (FR)

(73) Assignee: Centre de Pyrolyse du Charbon de Marienau, Forbach (FR)

( * ) Notice: Subject to any disclaimer, the term of this patent is extended or adjusted under 35 U.S.C. 154(b) by 0 days.

(21) Appl. No.: 16/313,130

(22) PCT Filed: Jun. 30, 2017

(86) PCT No.: PCT/IB2017/053970
§ 371 (c)(1),
(2) Date: Dec. 24, 2018

(87) PCT Pub. No.: WO2018/002900
PCT Pub. Date: Jan. 4, 2018

(65) Prior Publication Data
US 2019/0219389 A1    Jul. 18, 2019

(30) Foreign Application Priority Data

Jun. 30, 2016 (WO) .................. PCT/IB2017/053970

(51) Int. Cl.
*G01B 11/24* (2006.01)
*G01N 21/954* (2006.01)
(Continued)

(52) U.S. Cl.
CPC ............ *G01B 11/24* (2013.01); *C21C 5/4673* (2013.01); *F27D 21/0021* (2013.01);
(Continued)

(58) Field of Classification Search
CPC ...... F27D 21/00; F27D 21/0021; F27D 21/02; F27D 2021/023; F27D 2021/026;
(Continued)

(56) References Cited

U.S. PATENT DOCUMENTS 3,609,236 A * 9/1971 Heilman ................. F27D 21/02
348/83
4,616,694 A * 10/1986 Hsieh ..................... A62B 13/00
165/47
(Continued)

FOREIGN PATENT DOCUMENTS

IN  6972/CHENP/2010 A   4/2011
JP  H07208916 A   8/1995
(Continued)

OTHER PUBLICATIONS

Abstract and sole figure to CN 107502700 A published on Dec. 22, 2017. (Year: 2017).*

*Primary Examiner* — Gordon J Stock, Jr.
(74) *Attorney, Agent, or Firm* — Davidson, Davidson & Kappel, LLC (57) ABSTRACT

A device for measuring a shape of a wall portion of a coke oven is provided. The device includes a box having a main part defining at least one opening and a closing system movable with respect to the main part between an open position and a closed position, an internal protective screen located within the box and defining at least one scanning window, the scanning window being narrower than the opening along a transverse direction (T) of the box and at least one 3D laser scanner located in the box for scanning the wall portion through the scanning window and through the opening when the closing system is in the open position.

15 Claims, 9 Drawing Sheets

(51) Int. Cl.
  *F27D 21/00* (2006.01)
  *C21C 5/46* (2006.01)
  *F27D 21/02* (2006.01)
  *G01B 11/25* (2006.01)

(52) U.S. Cl.
  CPC .......... *F27D 21/02* (2013.01); *G01B 11/2518* (2013.01); *G01N 21/954* (2013.01)

(58) Field of Classification Search
  CPC .. G01N 21/954; G01N 21/88; G01N 21/8806; C21C 5/4673; G01B 11/022; G01B 11/024; G01B 11/026; G01B 11/24; G01B 11/25; G01B 11/2518; G01B 11/30; G01B 11/303; G01B 11/306
  See application file for complete search history.

(56) References Cited

U.S. PATENT DOCUMENTS

| | | | | |
|---|---|---|---|---|
| 4,893,933 A * | 1/1990 | Neiheisel | ................ | C21C 5/441 356/3.06 |
| 5,125,745 A * | 6/1992 | Neiheisel | ................ | C21C 5/441 356/602 |
| 5,212,738 A * | 5/1993 | Chande | ................... | C21C 5/441 348/135 |
| 5,394,208 A * | 2/1995 | Campbell | ............. | G03B 29/00 348/E5.026 |
| 5,745,969 A | 5/1998 | Yamada et al. | | |
| 6,002,993 A * | 12/1999 | Naito | ...................... | C10B 41/00 348/83 |
| 6,922,252 B2 * | 7/2005 | Harvill | ................... | G01B 11/00 356/614 |
| 8,311,777 B2 * | 11/2012 | Sugiura | .................. | C10B 29/06 356/2 |
| 8,345,266 B2 * | 1/2013 | Brzoska | .............. | F27D 21/0021 356/601 |
| 8,562,227 B2 * | 10/2013 | Kocanda | ............ | G05B 19/042 396/427 |
| 10,175,040 B2 * | 1/2019 | Bonin | ..................... | G01S 17/10 |
| 2007/0028469 A1 | 2/2007 | Nash et al. | | |
| 2012/0026510 A1 | 2/2012 | Crampton et al. | | |
| 2014/0340505 A1 * | 11/2014 | Olsson | ............... | G01N 21/8803 348/84 |
| 2019/0244343 A1 * | 8/2019 | Chuang | .................. | G01B 11/30 |

FOREIGN PATENT DOCUMENTS

| | | | | |
|---|---|---|---|---|
| JP | 2003207321 A | 7/2003 | | |
| JP | 4188919 B2 * | 12/2008 | ............ | C10B 33/10 |
| JP | 2014218557 A | 11/2014 | | |
| KR | 200282938 Y | 11/2002 | | |
| KR | 20080113338 A | 12/2008 | | |
| KR | 20130067792 A | 6/2013 | | |
| RU | 2052486 C1 | 1/1996 | | |
| SU | 1770346 | 10/1992 | | |
| WO | 2009119501 A1 | 10/2009 | | |
| WO | WO-2018109510 A1 * | 6/2018 | ............ | F27D 19/00 |

* cited by examiner

DEVICE FOR MEASURING A SHAPE OF A WALL PORTION OF A COKE OVEN

The present invention relates to a device for measuring a shape of a wall portion of a coke oven.

The present invention also relates to an installation comprising an oven and such a device, as well as to a method of measuring a shape of a wall portion of a coke oven.

The invention also relates to a method for scanning the entire left and right walls of the oven through an opening of the oven.

BACKGROUND OF THE INVENTION

Coke ovens are used to produce coke from charcoal in iron and steel industry. They are constituted by alternatively disposing coking chambers and combustion chambers separated by oven walls made of bricks. A coking chamber has a parallelepiped shape, usually between 3.5 and 8 meters high, between 12 and 20 meters deep along a horizontal direction, and between 0.35 and 0.7 meter wide. They usually comprise two opposite doors respectively at both ends along the horizontal direction.

The coking process involves carbonization of coal to high temperatures, above 1000° C., in an oxygen deficient atmosphere in order to concentrate the carbon. Coal is charged from a coal charging hole at a top portion of the coking chamber. Then, a high temperature of 1000° C. or more is applied to the coal inside the coking chamber for approximately 20 hours. Coal is thereby coked (carbonized), and coke cake (hereinafter, referred to as just "coke") is produced. When the coke is produced, doors disposed at both ends of the coking chamber are opened, the coke is pushed by a pusher from a lateral side of the coking chamber, and the coke is taken out of the coking chamber.

Apart from high temperatures, the coking process also generates a lot of dust, soot and steam.

When coal is transformed into coke, it exerts a high pressure onto the bricks of the oven wall which can then be deformed. These deformations of the oven walls may induce issues for pushing the coke out of the chamber and then increase damages of the oven walls. Moreover, the bricks are exposed to high temperature variations between oven loading and unloading and thermal shocks may occur, which also causes damages to the walls.

All these damages eventually alter the shape of the walls and impact the productivity of the coking plant by inducing issues during coal charging or coke pushing.

Measurements of the wall shape are performed after unloading and before the following loading. The wall temperature is typically in a 900° C. to 1000° C. range.

For this reason, there has been a need for monitoring the conditions of coke ovens, in particular in order to check whether the walls shape is not altered.

In the past, this was performed through visual inspection, but it involved a lot of safety risks for operators and was not very accurate.

Document JP2014-218557 describes using a 3D laser to assess the shape of the chamber wall. The laser is placed on a first location in front of a first door of the coking chamber so as to scan a portion of the left wall of the chamber. Then it is moved to a second location so as to scan a portion of the right wall of the chamber.

Besides, 3D laser scanners have been used in some other technical fields in order to measure three dimensional shapes. However, such scanners have been considered unfit for use within a coking plant, because they cannot withstand the hot, dusty and humid environment nearby running coke ovens.

BRIEF SUMMARY OF THE INVENTION

An object of the invention is to provide a device adapted for measuring a shape of a wall portion of an idle coke oven, and adapted for use nearby a running coke oven.

The present invention provides a device for measuring a shape of a wall portion of a coke oven, the device comprising:
 a box having a main part defining at least one opening and a closing system movable with respect to the main part between an open position and a closed position, wherein the box is water-tight and protected from dusts and external solid projections when the closing system is in the closed position,
 an internal protective screen located within the box and defining at least one scanning window, wherein the scanning window is narrower than the opening along a transverse direction of the box, and
 at least one 3D laser scanner located in the box for scanning said wall portion through the scanning window and through the opening when the closing system is in the open position, the laser scanner being configured for moving relative to the box in order to scan the wall portion.

In other embodiments, the device may comprise one or several of the following features, taken in isolation or any technical feasible combination:
 the internal protective screen comprises several modules distributed along the transverse direction, each module being adapted to reflect at least 70% of the thermal radiations coming from the oven substantially radially with respect to the transverse direction through the opening;
 the internal protective screen comprises two opposite extremal modules along the transverse direction, wherein each of the extremal modules is adapted to reflect at least 80% of the thermal radiations coming from the oven substantially along the transverse direction through the opening;
 the device comprises at least one gas spring adapted to hold the closing system in the open position, wherein at least one of the extremal modules is adapted to hide at least a portion of the gas spring from thermal radiations coming from the oven;
 the closing system comprises a cover rotatably mounted on the main part of the box;
 the cover includes an external protective panel adapted to reflect at least 80% of the thermal radiations coming from the oven when the closing system is in the closed position;
 the box has a rear face comprising fins directed outwardly in order to favor a thermal exchange between the box and the surrounding atmosphere;
 the device comprises at least one fan fixed to the rear face and adapted to blow or extract air on or from the fins;
 the device comprises a source of compressed air and at least one nozzle connected to said source of compressed air and adapted to blow air from the source of compressed air towards the 3D laser scanner;
 the device comprises a detector suitable for detecting when the closing system is in the open position, and a control unit in order to control the nozzle so that air from the source is blown towards the 3D laser scanner at least when the closing system is in the open position;

the device comprises a second 3D laser scanner, wherein said first and second 3D laser scanners are spaced apart from each other along the transverse direction and for example parallel to each other;

the 3D laser scanners are mounted on a same beam of the box; and the box is supported by, or fixed to, a plate rotatably mounted on a base.

The invention also provides an installation comprising a coke oven, and a device for measuring a shape of a wall portion as described above.

The invention further provides a method of measuring a shape of at least part of a chamber of a coke oven, the chamber having a left wall and a right wall opposed along the transverse direction of the oven, the method comprising at least the following steps:

providing a device as described hereabove, positioning the device in front of an opening of the oven, and at a distance with respect to said opening along a longitudinal direction perpendicular to the transverse direction, and transversely between the left wall and the right wall, and scanning the left wall and the right wall using the 3D laser scanner, wherein the laser scanner (21A) moves relative to the box (20) during scanning, without moving the device with respect to the oven during scanning.

BRIEF DESCRIPTION OF THE DRAWINGS

Other features and advantages of the invention will appear upon reading the following description, given by way of example and with reference to the accompanying drawings, in which.

DETAILED DESCRIPTION OF THE INVENTION

Figure 1:
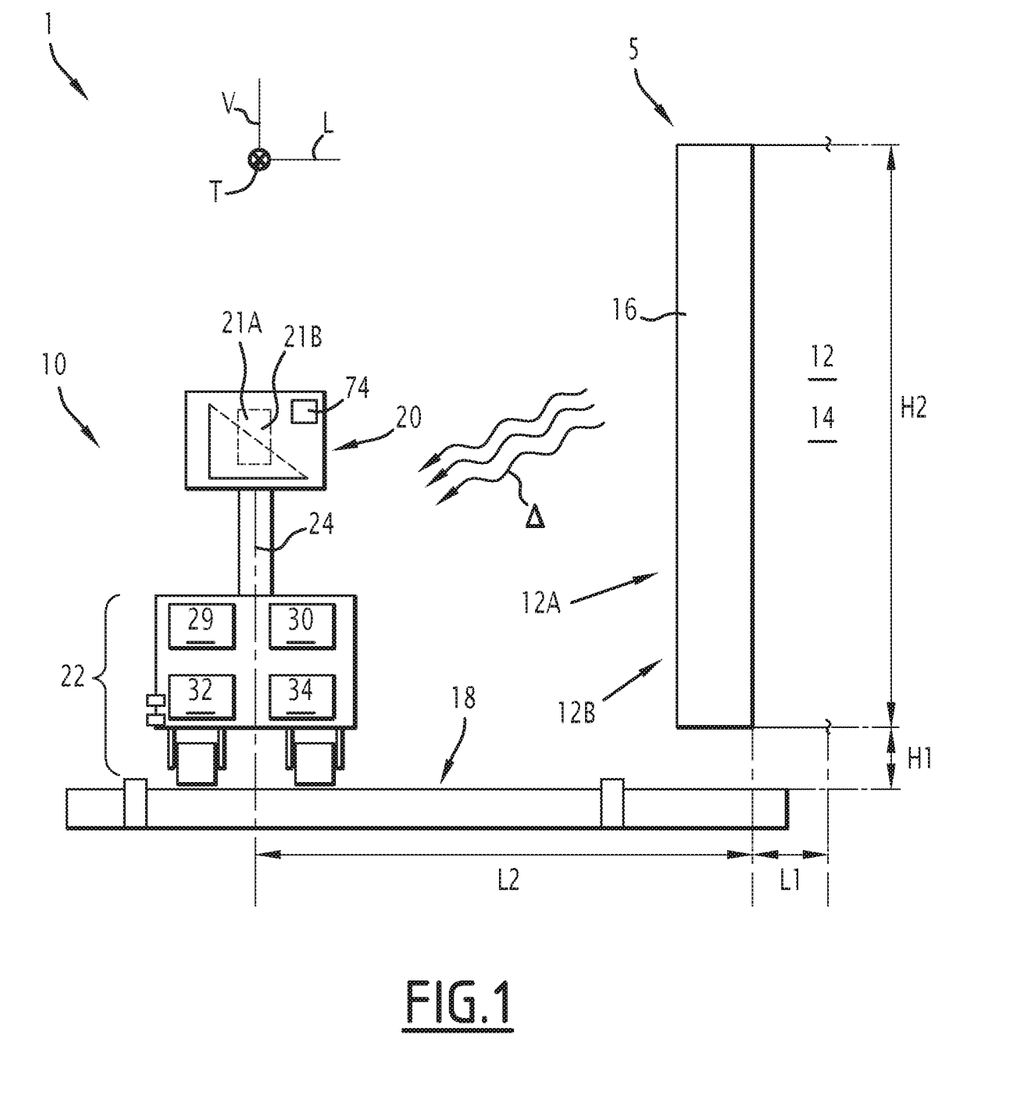
FIG. 1 is a schematic view of an installation according to the invention.
Figure 2:
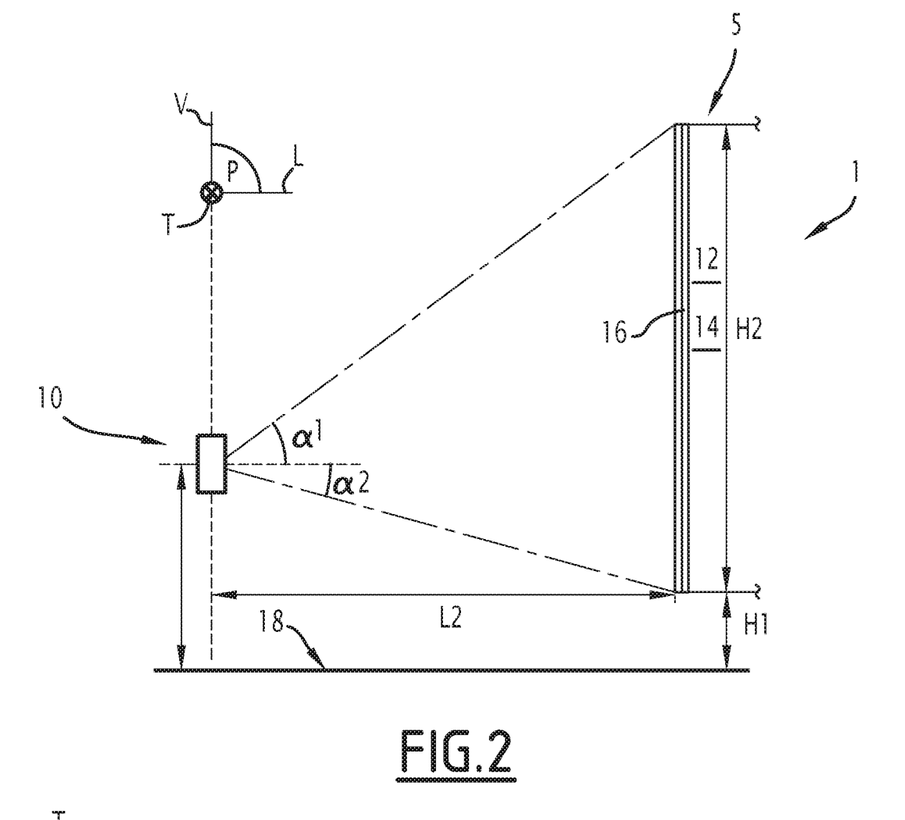
FIGS. 2 and 3 are schematic, respectively side and upper views of the installation shown in FIG. 1.

With reference to FIGS. 1 and 2, an installation 1 according to the invention is described.

The installation 1 comprises a coke oven 5 and a device 10 for measuring a shape of a wall portion 12 of the oven.

The oven 5 extends along a longitudinal direction L, for example approximately horizontal. The oven 5 defines a coking chamber 14 and has at least one door 16 facing the device 10 along the longitudinal direction L.

The door 16 defines an opening of the oven 5 and is intended to be open when the device 10 is running.

Figure 3:
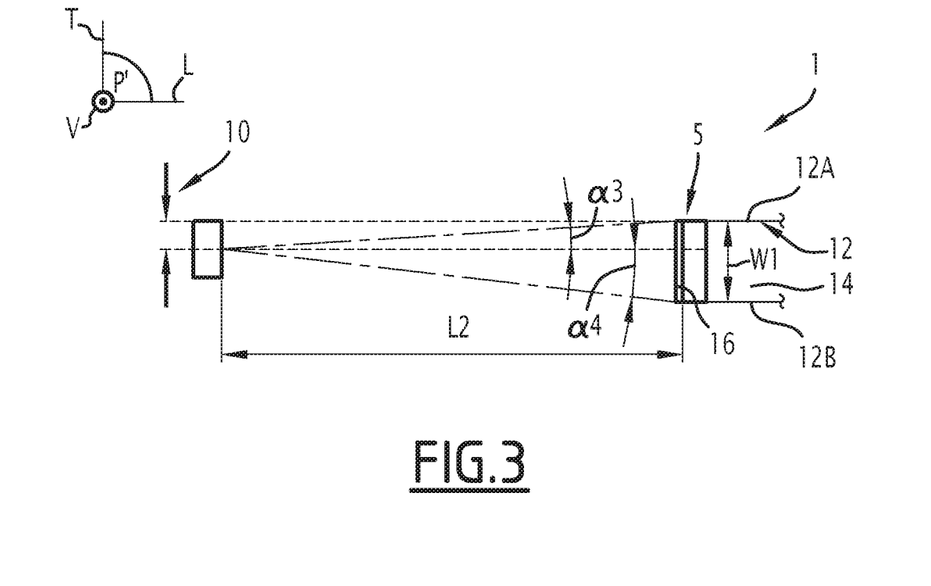

As also shown in FIGS. 2 and 3, the coking chamber 14 has a depth L1 along longitudinal direction L. The coking chamber 14 starts at a height H1 along a vertical direction V above a ground 18 on which the device 10 stands. The coking chamber 14 has a height H2 along the vertical direction V, and a width W1 along a transverse direction T that is perpendicular to the longitudinal direction L and to the vertical direction V. The chamber 14 has a left wall 12A and a right wall 12B along the transverse direction T.

For example L1 ranges between 12 and 20 meters.

For example H1 is up to 2 meter.

For example H2 ranges between 3.5 and 8 meters.

For example W1 ranges between 0.35 and 0.7 meter.

The wall 12 is for example substantially vertical and designed to be planar.

The wall portion is advantageously a two-dimensional surface.

The device 10 is adapted for measuring a shape of a portion of the wall 12, in order to advantageously detect whether the shape is locally concave or convex towards the interior of the coking chamber 14.

The device 10 is intended to be positioned outside the oven 5. Since the oven 5 may still have a high level of residual heat, this allows avoiding overly complex and expensive cooling members in the device 10.

Figure 4:
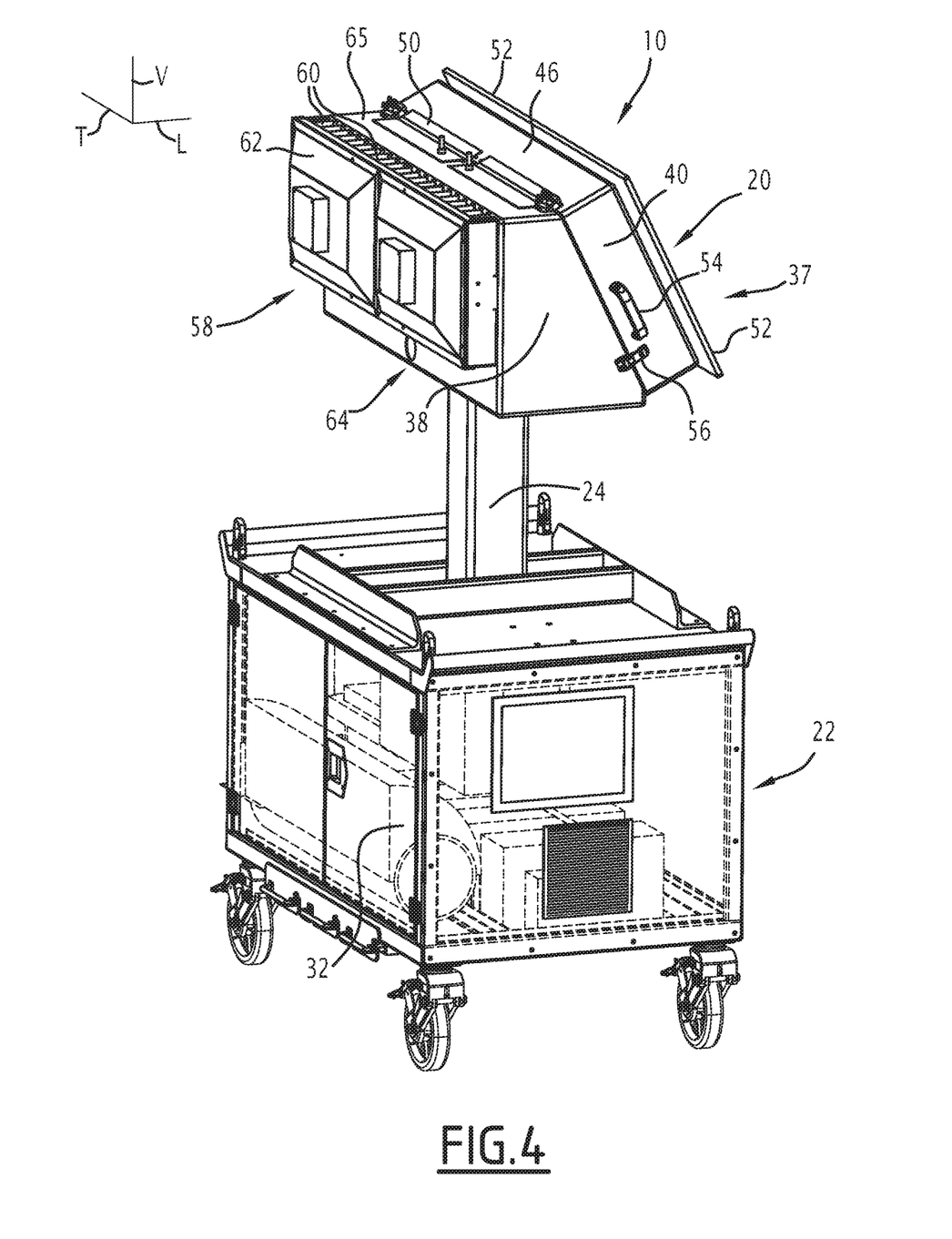
FIG. 4 is a perspective view of a device shown in FIGS. 1 to 3.

As best seen in FIGS. 1 and 4, in a first embodiment, the device 10 comprises a box 20, two 3D laser scanners 21A, 21B located within the box, a base 22, and a spacer 24 located vertically between the box and the base.

The base 22 is advantageously adapted to roll on the ground 18.

The base 22 includes a computer 29, a control unit 30 with one or several control screens, a source of compressed air 32, and a power source 34. The base 22 is advantageously equipped with one or several cooling fans having dust filters.

The base 22 and the spacer 24 are advantageously covered with a protective mat, notably on sides facing the oven 5. For example the mat comprises an aluminized glass fabric or any insulating material.

The power source 34 advantageously allows the device 10 being autonomous in terms of power supply. The power source 34 is for example an inverter. The source of compressed air 32 is for example a cylinder.

The computer 29 is suitable for monitoring the 3D laser scanners 21A, 21B.

Advantageously, the computer 29 includes one or several dedicated software(s) for analyzing the measurements performed by the 3D laser scanners 21A, 21B and for producing a report.

With reference to FIG. 4, the box 20 has a front face 37 facing the opening of the oven 5. The box 20 also comprises a main part 38 fixed to the base 22 by the spacer 24, and a closing system 40 movable with respect to the main part between a closed position (FIG. 4), wherein the box is closed around the 3D laser scanners 21A, 21B, and an open position (FIGS. 5 to 7), wherein the main part 38 defines at least one opening 44 in the front face 37. In particular embodiments, the box 20 is supported by, or fixed to, a plate rotatably mounted on the base 22, or the box is rotatably mounted on the base.

When the closing system 40 is in the closed position, the interior of the box 20 is protected against dust, and from water projections from all directions.

Figure 5:
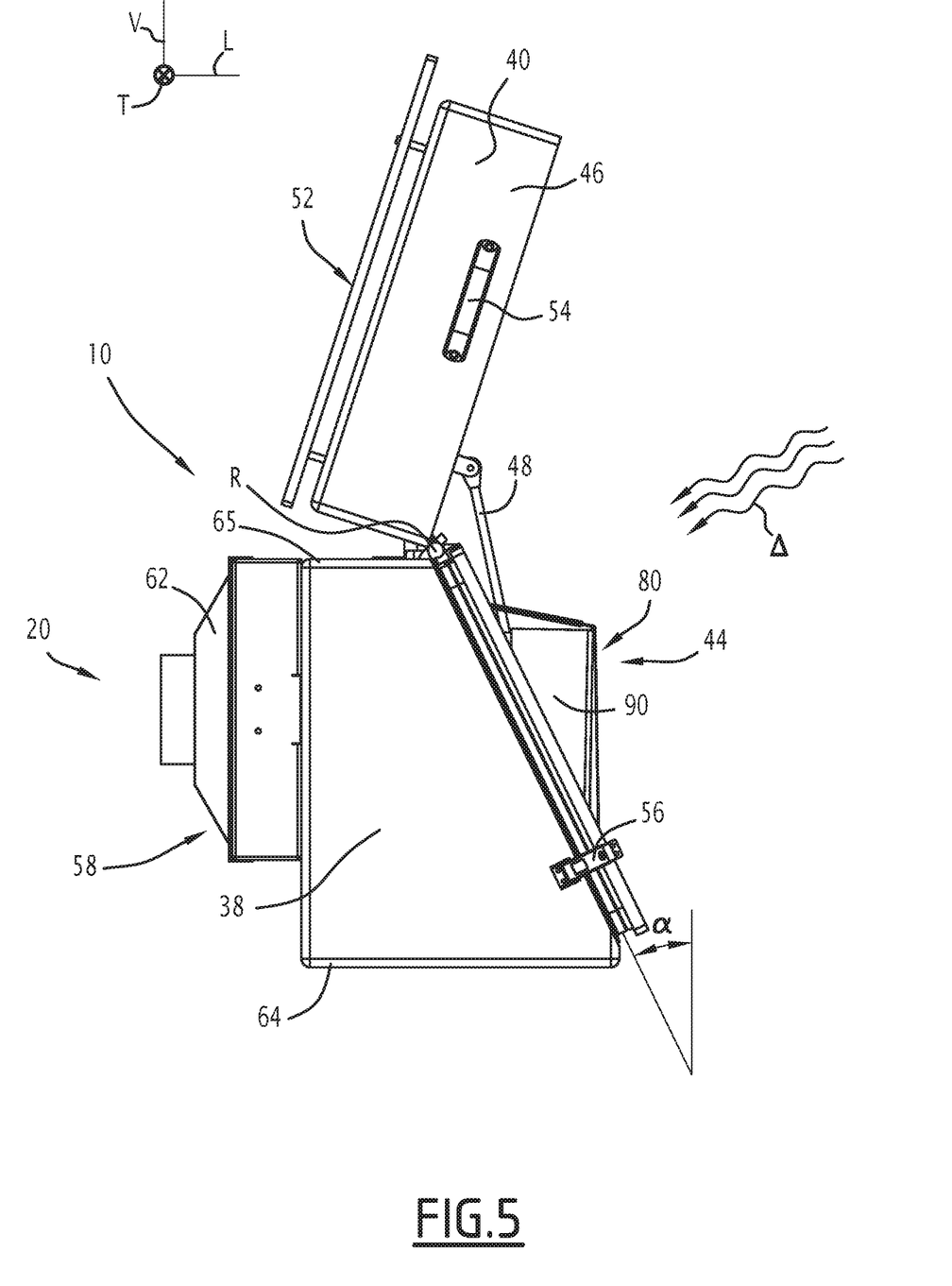
FIG. 5 is a side view of the box of the device shown in FIGS. 1 to 4.

The opening 44 in the front face 37 extends along the vertical direction V and along the transverse direction T. For example, the opening 44 has a planar, advantageously rectangular, shape. The opening 44 is advantageously parallel to the transverse direction T and for examples defines an angle α with the vertical direction V ranging between 45° and 80° (FIG. 5). Such an angle allows measuring the wall 12 over the entire height of the coking chamber 14.

Figure 6:
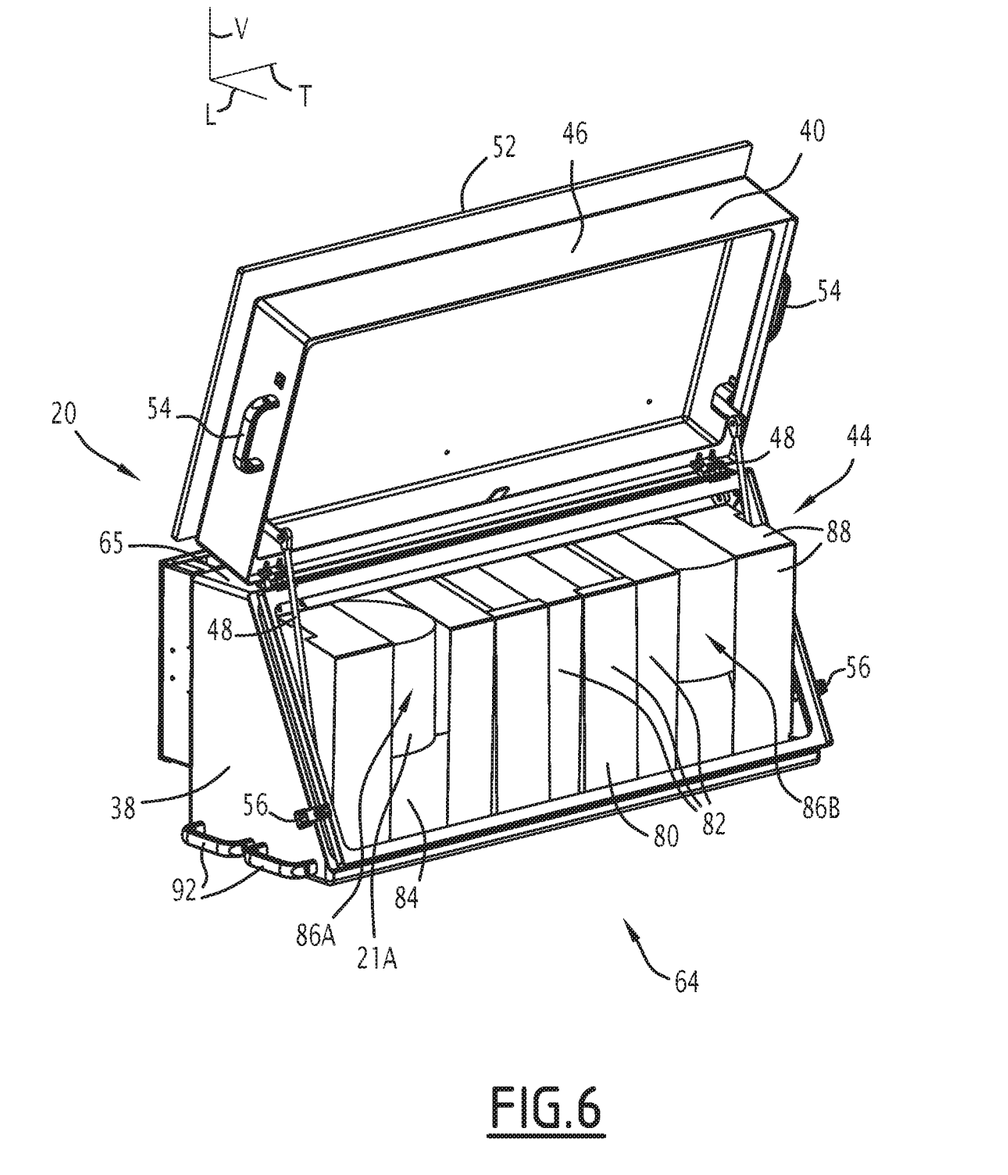
FIG. 6 is a perspective view towards a front face of the box shown in FIG. 5.
Figure 7:
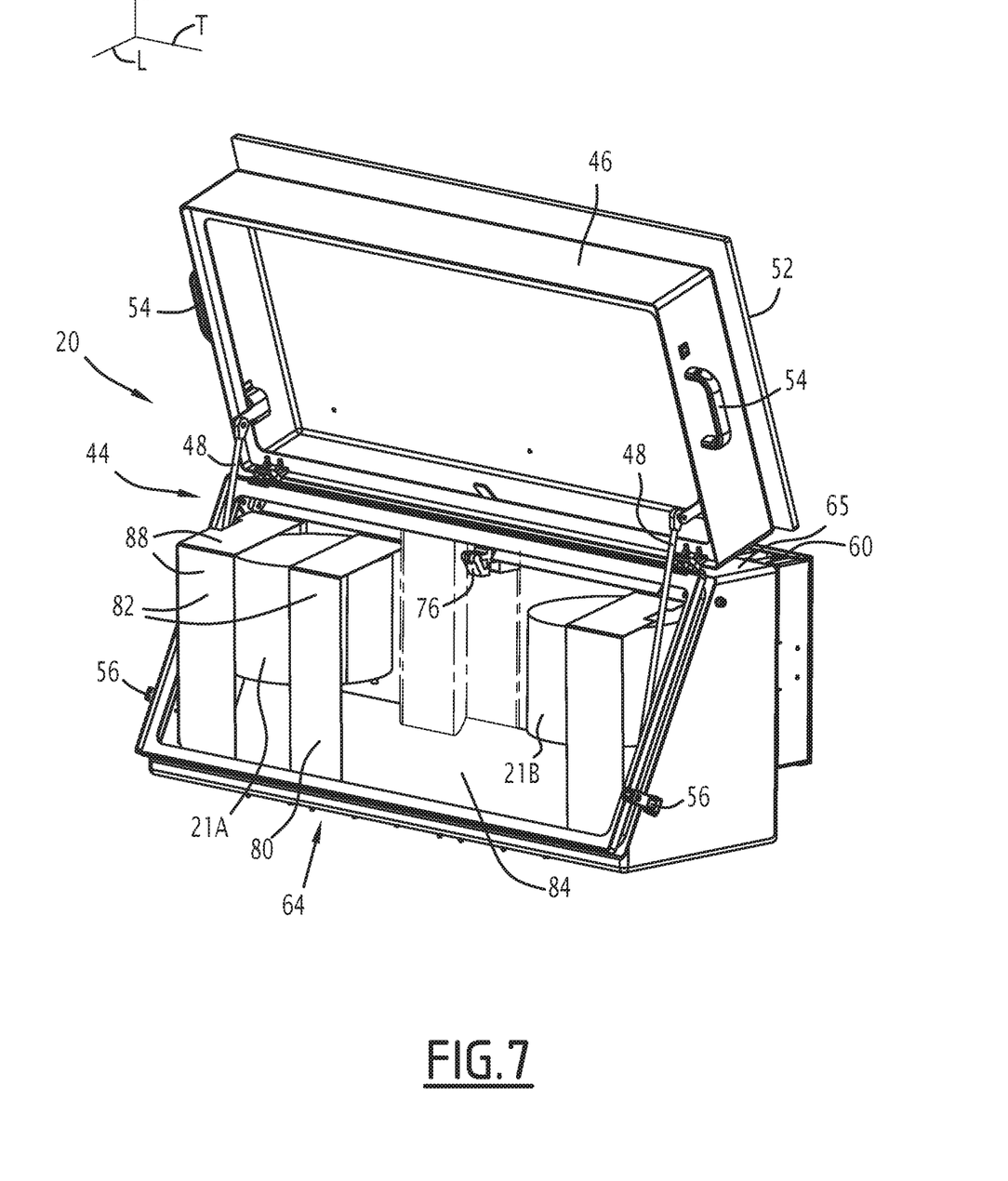
FIG. 7 is a different perspective view of the box shown in FIGS. 5 and 6, wherein some modules of the internal protective screen have been removed.

The closing system 40 comprises a cover 46 rotatably mounted on the main part 38 around an axis R (FIG. 5), and for example one or two gas springs 48 adapted to hold the cover in the open position as shown in FIGS. 5 to 7.

The closing system 40 advantageously includes a seal in fluoroelastomer installed between the cover 46 and the main part 38. Fluoroelastomer is a fluorocarbon-based synthetic rubber able to withstand a range of temperatures from −20° C. to 200° C.

As a variant, the seal includes a coating adapted for conducting heat towards the rear of the device 10, and for reflecting thermal radiations Δ from the oven 5.

By "adapted to reflect thermal radiations from the oven", in the present application, it is meant that the 3D laser scanners are protected from the thermal radiations emitted by the oven 5. The axis R is for example approximately parallel to the transverse direction T.

The cover 46 advantageously includes an upper flap 50 (FIG. 4) adapted to protect the interior of the box 20 from the outside dust.

The cover 46 advantageously includes an external protective panel 52 adapted to reflect thermal radiations Δ coming from the oven 5 when the closing system 40 is in the closed position.

In one embodiment the cover 46 is adapted to be manually moved in order to move the closing system 40 from the closed position to the open position, and vice versa. To that end the cover 46 advantageously comprises handles 54 and fasteners 56, for example hook clamps. In another embodiment the cover 46 is automatically controlled.

The protective panel 52 is for example made of reflective metal, such as stainless steel, polished stainless steel, aluminum or polished aluminum and may contain an insulating material such as ceramic fiber. The external protective panel 52 is advantageously spaced apart from the rest of the cover 46, as best seen on FIG. 5.

The main part 38 of the box 20 has a rear face 58 (FIG. 4) at the back of the box 20 with respect to the oven 5, advantageous having fins 60 directed outwardly in order to favor a thermal exchange between the box and the surrounding atmosphere.

In a particular embodiment, two fans 62 are fixed to the rear face 58 and adapted to blow or extract air on the fins 60 to increase the cooling.

The main part 38 also has a bottom wall 64, for example substantially flat, and advantageously forming a connection interface for mechanically connecting the box 20 and the spacer 24. The main part 38 has an upper wall 65.

Figure 8:
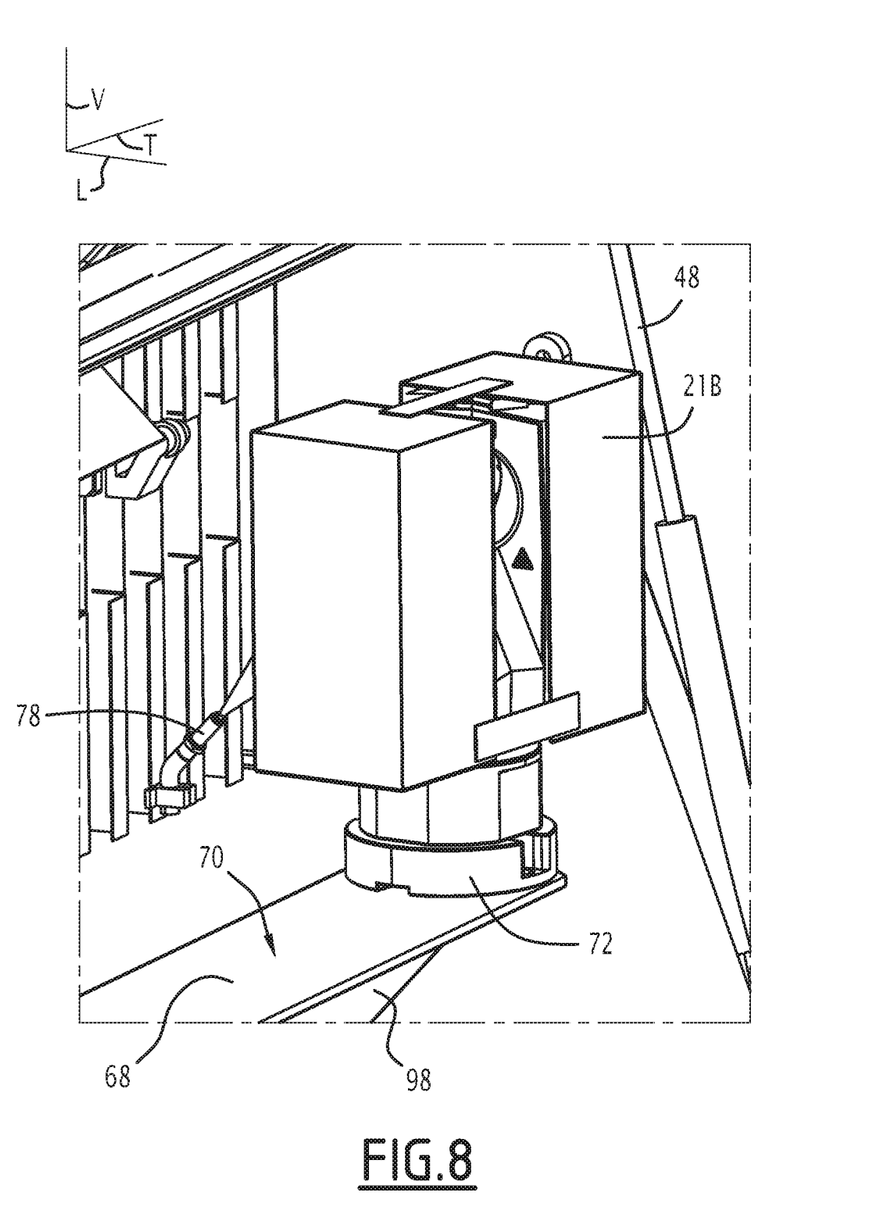
FIG. 8 is a perspective view of one of the 3D laser scanners of the device shown in FIGS. 1 to 7, and FIGS. 9 to 11 are graphs showing measurements performed on a coke oven at industrial scale.

The main part 38 comprises a beam 68 (FIG. 8), for example fixed to the bottom wall 64 towards the interior of the box 20, forming a platform 70 extending transversely and advantageously designed to be substantially parallel to the ground 18.

The main part 38 comprises two scanner adapters 72 fixed to the platform 70 and respectively serving as bases for the 3D laser scanners 21A, 21B.

The main part 38 comprises an acquisition module 74 (FIG. 1) for acquiring temperatures within the box 20.

The main part 38 advantageously includes a position detector 76 (FIG. 7) for detecting whether the closing system 40 is in the open position or in the closed position, and two nozzles 78 (FIG. 8) connected to the source of compressed air 32 for blowing compressed air respectively towards the 3D laser scanners 21A, 21B.

The device 10 also includes an internal protective screen 80 adapted to reflect at least 80% of the energy of the thermal radiations Δ coming from the oven 5 substantially radially with respect to the transverse direction T through the opening 44 of the front face 37.

The internal protective screen 80 for example comprises several modules 82 distributed along the transverse direction T, and optionally a transverse module 84 adapted to protect the beam 68 from the thermal radiations Δ.

The transverse module 84 is interposed between the beam 68 and the oven 5. The transverse module 84 extends transversely across the opening 44.

Each module 82 is adapted to reflect at least 70% of the energy of the thermal radiations Δ coming from the oven 5.

The modules 82 are advantageously fixed to the lower wall 64 and the upper wall 65 of the main part 38, for example by a few screws respectively, so as to be easily movable by an operator along the transverse direction T in order to define two scanning windows 86A, 86B respectively in front of the 3D laser scanners 21A, 21B, regardless of the position of the latter.

For example, each module 82 has an "L" shape along the transverse direction T. Each module 82 comprises two panels 88 forming the "L". One of the panels 88 is for example approximately perpendicular to the longitudinal direction L, and the other one is approximately perpendicular to the vertical direction V. The panels 88 are adapted to reflect thermal radiations Δ coming from the oven 5 substantially radially with respect to the transverse direction T through the opening 44.

Advantageously, among the modules 82, a module, for example central along the transverse direction T, is suitable for protecting the position detector 76, and two opposite extremal modules along the transverse direction T are suitable for at least partly protect the gas springs 48.

Advantageously, the modules 82 and the transverse module 84 comprise at least 50% in weight of polished aluminum.

For example the adapters 72 are movable between several positions, for example three, with respect to the platform 70 along the transverse direction T.

Several washers, for example those known as "Delrin washers", are interposed between the beam 68 and the lower wall 64 in order to limit thermal conduction.

The acquisition module 74 (FIG. 1) includes several temperature sensors spread within the box 20. Advantageously two temperature sensors are located on the beam 68 in the vicinity of the 3D laser scanners 21A, 21B. For example two temperature sensors are located on the lower wall 64 of the main part 38.

The 3D laser scanners 21A, 21B are fixed to the adapters 72 (FIG. 8) and mounted parallel to each other. The 3D laser scanners 21A, 21B are for example Focus$^{3D}$ laser scanners commercially available from Faro, or similar ones. The 3D laser scanners 21A, 21B are adapted to be monitored by the computer 29.

The 3D laser scanners 21A, 21B are advantageously protected with reflective adhesive tape stuck to their walls. The adhesive tape is advantageously in aluminized glass fabric, for example the one referenced 363 by the company 3M.

Each of the laser scanners 21A, 21B is for example adapted for emitting and receiving light through the scanning window.

Each of the laser scanners 21A, 21B is configured for moving relative to the box 20 in order to scan the wall portion 12.

The 3D laser scanners 21A, 21B are located at a distance L2 from the coking chamber 14 (FIGS. 1 to 3), for example ranging between 1 and 4 meters.

The 3D laser scanners 21A, 21B are adapted to scan the coking chamber 14 in a vertical plane P (FIG. 2) from an upper angle α1 to a lower angle α2 with respect to the longitudinal direction L, and in a horizontal plane P' (FIG. 3) from a left angle α3 to a right angle α4 with respect to the longitudinal direction L.

The box 20 and the 3D laser scanners 21A, 21B are configured to scan most of the existing coking ovens. To that end, the box 20 and the 3D laser scanners 21A, 21B are designed in order to allow:

a maximum value of the upper angle α1 of 78°,
a maximum value of the lower angle α2 of at least 38.5°,
a maximum value of the left angle α3 of at least 13.5°, and
a maximum value of the right angle α4 of at least 30°.

These angles are optimized in order to reduce the scanning time and to allow scanning all the left wall 12A and the right wall 12B.

Such a length allows selecting the spacer 24 from a plurality of spacers having various lengths along the vertical direction V, in order to put the 3D laser scanners 21A, 21B at an adequate height. If H1 was above 1 meter, for example approximately 1.5 meter, a larger spacer or an additional spacer could be used between the base 22 and the box 20.

As a variant of the device 10, there is only one 3D laser scanner in the box 20, such as the laser scanner 21A. In this variant, there is only one scanner adapter 72 fixed to the platform 70 and one nozzle 78. The modules 82 defines only one scanning windows 86A.

A use of the invention will now be described.
It comprises the following steps:
providing the device 10,
turning the front face 37 of the box 20 towards the opening of the oven 5,
putting the closing system 40 in the open position, and scanning said wall portion 12 with the 3D laser scanners 21A, 21B through the opening 44 of the front face 37.

The positions of the 3D laser scanners 21A, 21B are selected depending on the dimensions of the oven 5, particularly the width W1 and the distance L2.

The modules 82, 84 of the internal protective screen 80 are fixed to the rest of the box 20 depending on the position of the 3D laser scanners 21A, 21B with respect to the beam 68 so as to define the scanning windows 86A, 86B (FIG. 6) within the opening 44.

The step of turning the front face 37 towards the oven 5 includes a substep of bringing the device 10 in front of the oven 5 at the distance L2 as shown in FIGS. 1 to 3, and a substep of selecting the adequate spacer 24 depending on the height H1.

The optional rotating plate allows aligning the box 20 with respect to the oven 5, so that the wall portion 12 can be scanned. For example, the orientation of the box 20 with respect to the vertical direction V can be monitored.

As long as the closing system 40 is in the closed position, all the elements inside the box 20 are well protected from thermal radiations Δ coming from the oven 5, and dust.

The external protective panel 52 allows leaving the device 10 in front of the oven 5 for some time, for example 5 minutes, without experiencing a temperature increase in the interior of the box 20 that could damage for example the 3D laser scanners 21A, 21B. Also, some heat is evacuated through the rear face 58 of the box 20, due to fins 60. Advantageously, the fans 62 are switched on in order to boost heat exchange through the rear face 58.

Similarly, the protective mats on the base 22 and on the spacer 24 delay the temperature increase of these elements. The cooling fans of the base 22 also contribute to keep the temperature inside the base 22 at an acceptable level, preferably below 40° C.

Due to the on board power source 34 and the source of compressed air 32, the device 10 is autonomous.

In order to perform the scan of the wall portion 12, the cover 46 is open manually. This puts the closing system 40 in the open position shown in FIG. 5. The handles 54 allow minimizing the exposure of the operator to the thermal radiations Δ during opening or closing of the cover 46.

The cover 46 is maintained by the gas springs 48 in the open or closed positions, both being stable.

The position detector 76 (FIG. 7) detects that the closing system has left the closed position and triggers the nozzles 78 (FIG. 8) to blow air towards the 3D laser scanners 21A, 21B.

The 3D laser scanners 21A, 21B are monitored by the computer 29 in order to scan the wall portion 12 through the opening 44 in the front face 37 and deliver signals representative of the shape of the wall portion in a way known in itself. The signals are then interpreted by the computer 29 and converted into data representative of the shape, for example a graph. During scanning, the device 10 is not moved with respect to the oven 5 and the adapters 72 are also in a fixed position.

In a particular embodiment, the entire left wall 12A and the entire right wall 12B are scanned by the 3D laser scanners without moving the device 10 with respect to the oven 5 during scanning.

In order to minimize the temperature increase in the device 10, the duration of the scan is minimized, and preferably kept lower than 3 minutes.

The temperature inside the box 20 is measured by the acquisition module 74 and sent to the computer 29.

The internal protective screen 80, by defining the scanning windows 86A, 86B, confines the laser beams emitted by the 3D laser scanners 21A, 21B in a useful solid angle shown in FIGS. 2 and 3. In particular, no laser beam can be emitted sideways, along the transverse direction T.

The internal protective screen 80 protects the laser scanners 21A, 21B and the gas springs from the thermal radiations Δ. The internal protective screen 80 limits the heat flux which enters the box 20 when the closing system 40 is in the open position. The internal protective screen 80 also limits the entry of outside air towards the interior of the box 20.

The flap 50 prevents the largest pieces of dust from entering the slot between the cover 46 and the main part 38 of the box 20.

The results of the scan are interpreted either just after the oven 5 has been scanned, or after all the ovens of a predetermined set have been scanned. Between the scans of two successive ovens, there is usually a waiting time of 8 to 12 minutes.

Due to the base 22, moving the device 10 in front of each oven successively is easy.

Due to the above mentioned features, the device 10 measures a shape of the wall portion 12 of the oven 5, and is particularly fit for use in presence of dust and thermal radiations, as well as nearby a running oven next to the oven 5.

The device 10 is also adapted for measuring a shape of a wall portion of any narrow oven having a great length, for example greater than 5 times the largest transverse dimension of the oven.

INDUSTRIAL TESTING

Industrial tests of the device 10 were performed confidentially on coke ovens in Dunkirk, France. The device 10 was positioned at 2.5 m from each oven entrance. The scanning phase took about 2.5 minute for each oven and gave very accurate results. Some of these results, obtained with a given oven, are shown in FIGS. 9 to 11.

Figure 9:
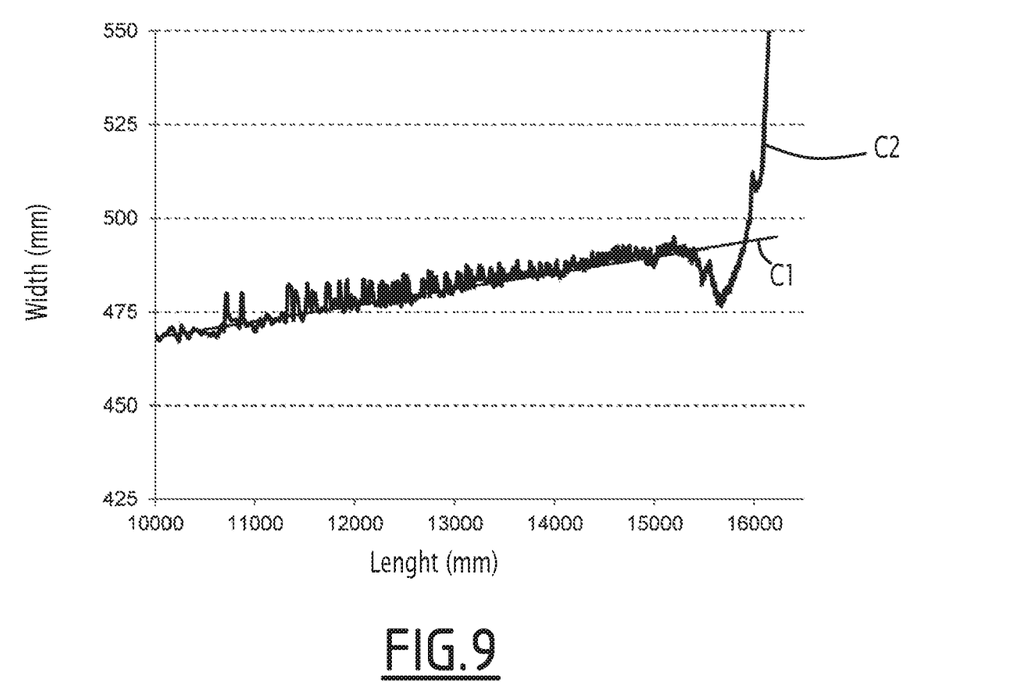
Figure 10:
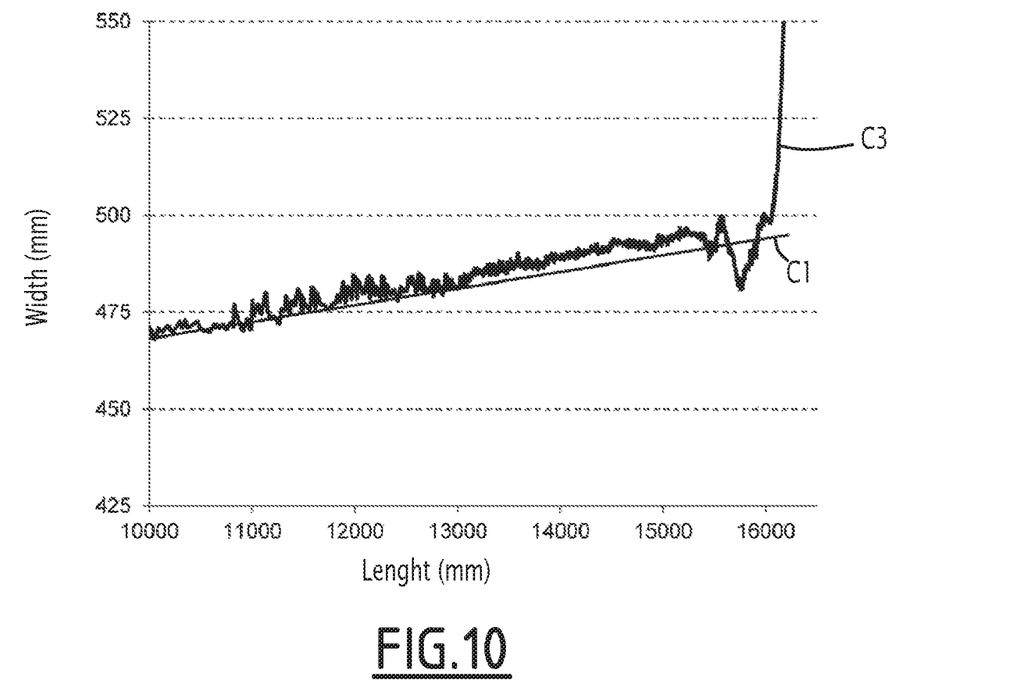
Figure 11:
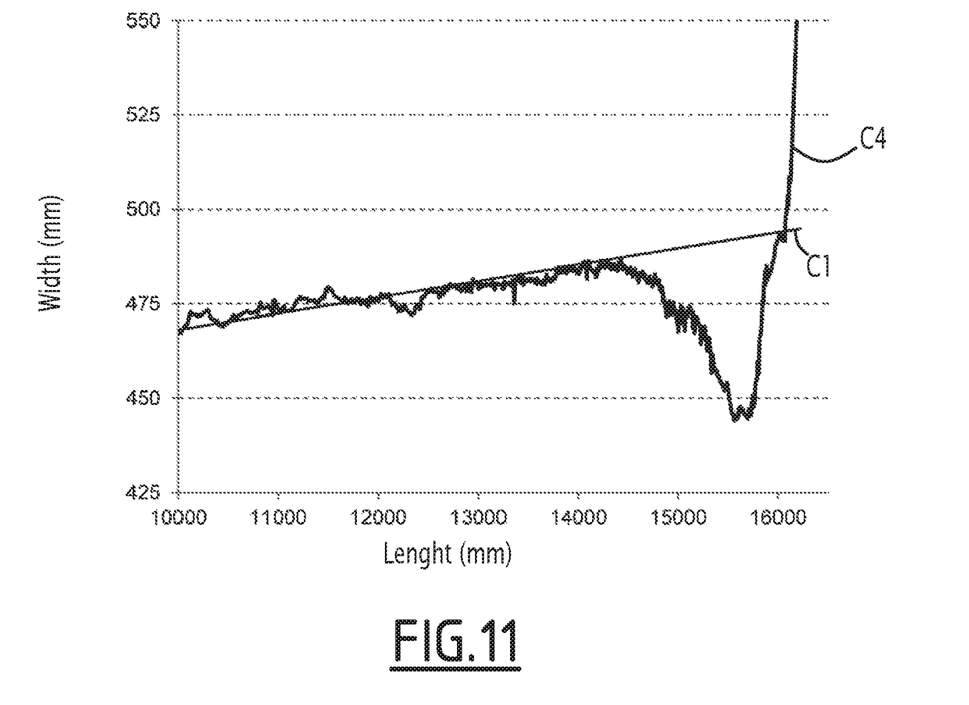

FIGS. 9 to 11 show the measured width (Y axis of the figures) of the oven along the transverse direction T versus the oven length (X axis of the figures) along the longitudinal direction L.

Curve C1 is the expected width profile of the oven.

Curves C2, C3 and C4 are the measured width profiles respectively at 10%, 50% and 90% of the height of the coking chamber 14 starting from its bottom.

FIGS. 9 to 11 allowed assessing how the measured width profiles C2 to C4 differ from the expected width profile C1.

Using these data, it was possible to relate the measured deviations to actual carbon deposit or brick displacements in the oven, and to explain why some of the ovens were easier to load or unload.

What is claimed is:

1. A device for measuring a shape of a wall portion of a coke oven, the device comprising:
    a box and at least one 3D laser scanner located in the box, the box having a front face configured to face an opening of a coke oven, a main part, and a closing system movable with respect to the main part between an open position, wherein the main part defines at least one opening in the front face, and a closed position, wherein the box is closed around the at least one 3D laser scanner and the box is water-tight and protected from dust and external solid projections; and
    an internal protective screen located within the box and defining at least one scanning window, wherein the scanning window is narrower than the opening along a transverse direction of the box;
    wherein the at least one 3D laser scanner is adapted for scanning a wall portion through the scanning window and through the opening when the closing system is in the open position, the laser scanner being configured for moving relative to the box in order to scan the wall portion.

2. The device according to claim 1, wherein the internal protective screen comprises several modules distributed along the transverse direction, each module being adapted to reflect at least 70% of the thermal radiations coming from the oven radially with respect to the transverse direction through the opening.

3. The device according to claim 2, wherein the internal protective screen comprises two opposite extremal modules along the transverse direction, wherein each of the extremal modules is adapted to reflect at least 80% of the thermal radiations coming from the oven along the transverse direction through the opening.

4. The device according to claim 3, further comprising at least one gas spring adapted to hold the closing system in the open position, wherein at least one of the extremal modules is adapted to hide at least a portion of the gas spring from thermal radiations coming from the oven.

5. The device according to claim 1, wherein the closing system comprises a cover rotatably mounted on the main part of the box.

6. The device according to claim 5, wherein the cover includes an external protective panel adapted to reflect at least 80% of the thermal radiations coming from the oven when the closing system is in the closed position.

7. The device according to claim 1, wherein the box has a rear face comprising fins directed outwardly in order to favor a thermal exchange between the box and the surrounding atmosphere.

8. The device according to claim 7, further comprising at least one fan fixed to the rear face and adapted to blow or extract air on or from the fins.

9. The device according to claim 1, further comprising a source of compressed air and at least one nozzle connected to the source of compressed air and adapted to blow air from the source of compressed air towards the 3D laser scanner.

10. The device according to claim 9, further comprising a detector suitable for detecting when the closing system is in the open position, and a control unit in order to control the nozzle so that air from the source is blown towards the 3D laser scanner at least when the closing system is in the open position.

11. The device according to claim 1, further comprising a second 3D laser scanner, wherein the first and second 3D laser scanners are spaced apart from each other along the transverse direction and for example parallel to each other.

12. The device according to claim 11, wherein the 3D laser scanners are mounted on a same beam of the box.

13. The device according to claim 1, wherein the box is supported by, or fixed to, a plate rotatably mounted on a base.

14. An installation comprising:
    a coke oven; and
    a device for measuring a shape of a wall portion of the coke oven according to claim 1.

15. A method of measuring a shape of at least part of a chamber of a coke oven, the chamber having a left wall and a right wall opposed along the transverse direction of the oven, the method comprising the steps of:
    providing a device for measuring a shape of a wall portion of a coke oven according to claim 1;
    positioning the device in front of an opening of the oven, at a distance with respect to the opening along a longitudinal direction perpendicular to the transverse direction, and transversely between the left wall and the right wall; and
    scanning the left wall and the right wall using the 3D laser scanner, wherein the laser scanner moves relative to the box during scanning, without moving the device with respect to the oven during scanning.

* * * * *